United States Patent [19]

Yang

[11] Patent Number: 5,589,117
[45] Date of Patent: Dec. 31, 1996

[54] INTEGRATED ABSORBENT STRUCTURES WITH DENSITY AND LIQUID AFFINITY GRADIENTS AND METHODS FOR MAKING THE SAME

[75] Inventor: Ching-Yun M. Yang, Princeton Junction, N.J.

[73] Assignee: McNeil-PPC, Inc., Skillman, N.J.

[21] Appl. No.: 495,740

[22] Filed: Jun. 8, 1995

Related U.S. Application Data

[62] Division of Ser. No. 176,747, Jan. 3, 1994, Pat. No. 5,525,407.

[51] Int. Cl.$^6$ ........................................................ B27N 3/04
[52] U.S. Cl. ................................................ 264/113; 264/518
[58] Field of Search ....................................... 264/113, 518, 264/510, 119

[56] References Cited

U.S. PATENT DOCUMENTS

| | | | |
|---|---|---|---|
| 4,276,338 | 6/1981 | Ludwa et al. | 428/218 |
| 4,677,018 | 6/1987 | L'Eprevier et al. | 428/218 |
| 4,699,823 | 10/1987 | Hellenberger et al. | 428/218 |
| 4,834,735 | 5/1989 | Alemany et al. | 428/218 |
| 5,079,074 | 1/1992 | Steagall et al. | 428/218 |
| 5,134,007 | 7/1992 | Reising et al. | 428/218 |
| 5,143,680 | 9/1992 | Molnar et al. | 264/511 |
| 5,294,478 | 3/1994 | Wanek et al. | 428/218 |

*Primary Examiner*—Mary Lynn Theisen
*Attorney, Agent, or Firm*—James P. Barr

[57] ABSTRACT

There is provided by this invention a least three integrated regions, each region having wherein the density and fluid affinity of the composite continuously increases from top to bottom thereby facilitating effective fluid transport and efficient utilization of storage capacity. An additional layer of SA and tissue may be provided to the absorbent product to provide an absorbent structure with dry feel and low stain. Methods of forming integrated, multi-layered absorbent composites and structures comprising at least three regions wherein each region has distinct density and fluid affinity gradients and wherein the density and fluid affinity of the composite continuously increases from top to bottom, are also provided herein.

6 Claims, 8 Drawing Sheets

CROSS-SECTION OF ENGINEERED ABSORBANT STRUCTURE

TRANSFER LAYER

9% TW FABRIC
80 / 20 ENKA / PULP
0.1 G / C. C. DENSITY

RECEIVING LAYER

55% TW FABRIC
12 / 88 ENKA / PULP
0.09 G / C. C. DENSITY

WICKING LAYER

36% TW FABRIC
6 / 94 ENKA / PULP
0.24 G / C. C. DENSITY

STORAGE LAYER 0.5 G SA / PAD
+

INTEGRATED ABSORBENT STRUCTURES WITH DENSITY AND LIQUID AFFINITY GRADIENTS AND METHODS FOR MAKING THE SAME

This is a division of application Ser. No. 08/176,747, filed Jan. 3, 1994, now U.S. Pat. No. 5,525,407 which is hereby incorporated by reference.

FIELD OF THE INVENTION

The present invention relates to absorbent products, especially absorbent structures with continuously increasing density and liquid affinity gradients, and methods and apparatus for making the same.

BACKGROUND OF THE INVENTION

There is a continuing effort to improve absorbent products, such as diapers, sanitary napkins, wound dressings, bandages, incontinent pads and the like that absorb body fluids, contain them well without leakage, and minimize skin wetness that can cause irritation. Generally, it is preferred that such absorbent products be soft and readily conform to body contours.

Many earlier absorbent products, in particular, diapers and sanitary napkins, contained an absorbent batt comprising tissue wadding or plies of paper tissue disposed between an impermeable backing sheet and a moisture permeable body facing sheet. The tissue wadding was not particularly desirable because it lacked a high absorptive capacity and imparted stiffness to the product.

Tissue wadding was replaced by a layer of individualized fluffed wood pulp fibers generally uniformly dispersed throughout the batt, such as that disclosed in U.S. Pat. No. 2,788,003. The fluffed wood pulp fibers provide a soft, high bulk, conformable product with an absorptive capacity and containment ability exceeding that of tissue wadding. However, although fluffed wood pulp fibers increase the fluid capacity of absorbent pads, the efficiency with which the capacity is used remains poor. This is because uniformly dispersed pulp does not effectively transport fluid away from areas of localized concentration. Body fluids are generally deposited in a localized area at or near the point of discharge and will follow a path of least resistance, which is usually the closest edge of the batt where fluid is no longer contained. This is particularly true when the absorbent product has an impermeable backing sheet because then the only path for fluid to escape is via the edges. Thus, the ineffective moisture conducting powers of a uniformly dispersed wood pulp batt contribute to the product's susceptibility to leaks.

The recognition that densified pulp is able to transport fluid effectively prompted the development of multilayered absorbent products wherein the various layers of the product are of different densities. See Burgeni and Kapur, "Capillary Sorption Equilibria in Fiber Masses," Test Res. J. 37(5):356 (1976) In manufacturing such a product, the various layers may be made separately, for example, by compression, and then combined to one structure with a capillary gradient. A traditional layered structure wherein a high density cotton core is wrapped with a loose, low density cotton fiber, is disclosed in U.S. Pat. No. 3,771,525. Another layered structure is shown in U.S. Pat. No. 3,017,304, which discloses an absorbent product containing a densified, paper-like layer. The paper-like layer acts as a wick so that liquid placed on this layer tends to move rapidly along the plane line of the layer. The paper-layer concept was used to improve the absorptive efficiency of the fluffed wood pulp fiber.

As well known to those of ordinary skill, the concept of combining a wicking layer with fluffed wood pulp fibers has gained wide acceptance in many absorbent products. For example, a diaper which incorporates this paper-like layer combined with fluffed wood pulp is disclosed in U.S. Pat. No. 3,612,055. This diaper construction is described as keeping moisture away from an infant's skin, while at the same time handling a full volume discharge of urine. The diaper is a multi-layer diaper comprising a fibrous facing layer in the form of a homogenous blend of short and long fibers which is brought into contact with the infant's skin, a layer of highly porous, loosely compacted cellulosic batt, a paper-like densified, highly compacted cellulosic fibrous layer integral with the loosely compacted batt, and an impervious backing sheet adhered to the densified layer throughout the interface with the densified layer.

A method of manufacturing a self-sustaining absorbent fabric is disclosed in U.S. Pat. No. 4,134,948. This method provides an absorbent fabric comprising an air laid, randomly arranged, intermingled cellulosic fibrous batt having a plurality of high loft, loosely compacted regions separated from each other by highly compressed regions. The compressed regions are formed by moistening the batt, embossing the batt for providing a pattern in the surface, and applying an adhesive material to the patterned surface. The adhesive penetrates through the compressed regions to form bonded fiber networks and partially penetrates through the high loft absorbent regions. The highly compressed regions have high capillary forces which aid in transmitting fluids along the fibrous structure, and the unbonded interiors of the high loft regions provide high capacity regions for storing such fluids.

Unfortunately, the fluffed wood pulp products discussed above do little to minimize potentially irritating skin wetness. U.S. Pat. No. 3,768,480 discloses an absorbent product wherein the facing layer has a wettability gradient that gradually increases within the facing layer to promote flow of fluid through the facing layer and into the batt, thereby providing a relative dry surface in contact with the skin. The wettability gradient is achieved by gradually decreasing the proportion of long fibers and increasing the level of short fibers in a blend, with the greatest concentration of long fibers being adjacent to the outer face of the facing layer, and with the concentration of short cellulosic fibers gradually increasing from the outer face to the inner face adjacent to the batt.

Even though the above-described products make much greater use of the capacity of the absorbent batt, none of them totally contain the absorbed liquid. It is probable that these products will leak before the full capacity of the batt is used for absorption. Although the recently introduced elastic leg or stretch diapers, such as those disclosed in U.S. Pat. Nos. 3,860,003, 4,050,462, and 4,324,245, improve containment of liquid, the elasticized portion itself can be irritating to the skin. Moreover, because the products fit more tightly, less air circulation is permitted which also enhances irritation.

The addition of superabsorbents into the storage zone of the product further improves the performance of the absorbent product. Superabsorbent materials are materials which will absorb many times their weight of liquid. U.S. Pat. No. 4,540,454, discloses a relatively thin absorbent product that utilizes superabsorbents. The product comprises a wicking layer and an absorptive layer superimposed upon one another, for example, by air layering. The absorptive layer is a low density, resilient, fibrous web consisting of randomly disposed, frictionally entangled fibers, resulting in a web having a dry bulk recovery of at least sixty percent, an initial dry bulk of at least 20 cc/gm and a weight less than about 2 oz/yd. The fibrous web is used to spatially distribute superabsorbent material so that upon exposure to an aqueous material, swelling occurs with minimal interference from adjacent superabsorbing material. The wicking layer is a high density transporting structure made of particles such as cellulosic fibers and/or peat moss. The layers are compressed at a pressure adequate to collapse the entire structure to provide intimate contact between the two layers and a structure that is one-half its original thickness.

It is well known that absorptive materials with low density have great liquid retaining capacity but poor liquid transmitting capacity, whereas absorptive materials with high density have great liquid transmitting capacity but poor liquid retaining capacity. It is also well known that flow and diffusion in capillary systems takes place in the direction from large capillaries (areas having absorptive materials with low density) to small capillaries (areas having absorptive materials with high density). In attempts to attain a balance between liquid retaining and liquid transmitting properties, and to maximize utilization of absorptive materials, prior art absorbent structures have included various layers of mutually differing densities.

U.S. Pat. No. 4,818,315, discloses a method of manufacturing a fibrous absorptive body having a continuous density gradient. In this method, absorptive fibers and a thermoplastic binding agent are formed into a homogenous intermixture in the form of a non-compressed web. The web is heated at a temperature above the melting point of a bonding fiber to activate the binding agent and thereby interconnect the absorptive fibers. The web is then cooled to a temperature below the binding temperature of the binding agent, and subsequently compressed between two rollers. One of the two rollers is at a temperature below the binding temperature of the binding agent and the other of the two rollers is at a temperature above the binding temperature of the binding agent. The desired effect is that binding decreases in a direction away from the opposite side of the web so as to produce a continuous density gradient in the web after its passage between the two rollers.

Recently, research has focused on providing a thin absorbent product that effectively transports fluid away from the body facing layer and utilizes its storage capacity efficiently. Despite the advent of many new thin absorbent products and methods for making the same, currently available products continue to exhibit problems such as leakage, staining, skin wetness and irritation. Accordingly, there is a need for improved absorbent structures that effectively transport fluid away from the body facing layer and utilize storage capacity efficiently.

SUMMARY OF THE INVENTION

There is provided by this invention a multi-layered absorbent composite comprising at least three integrated regions, each region having distinct density and fluid affinity gradients, wherein the density and fluid affinity of the composite continuously increases from top to bottom of the composite thereby facilitating effective fluid transport and efficient utilization of storage capacity.

There is also provided by this invention a multi-layered absorbent structure comprising a multi-layered absorbent composite having continuously increasing density and fluid affinity gradients and a layer of superabsorbent and/or a layer of tissue.

Methods of forming integrated, multi-layered absorbent composites and structures wherein the composites and structures have at least three distinct density and fluid affinity gradients and wherein the density and fluid affinity of the composites and structures continuously increase from top to bottom, are also provided.

BRIEF DESCRIPTION OF THE DRAWINGS

FIG. 1b is a cross section of the receiving layer measured by the Gravimetric Absorbency Tester as presented in FIG. 1a.

DETAILED DESCRIPTION OF THE INVENTION

Figure 1A:
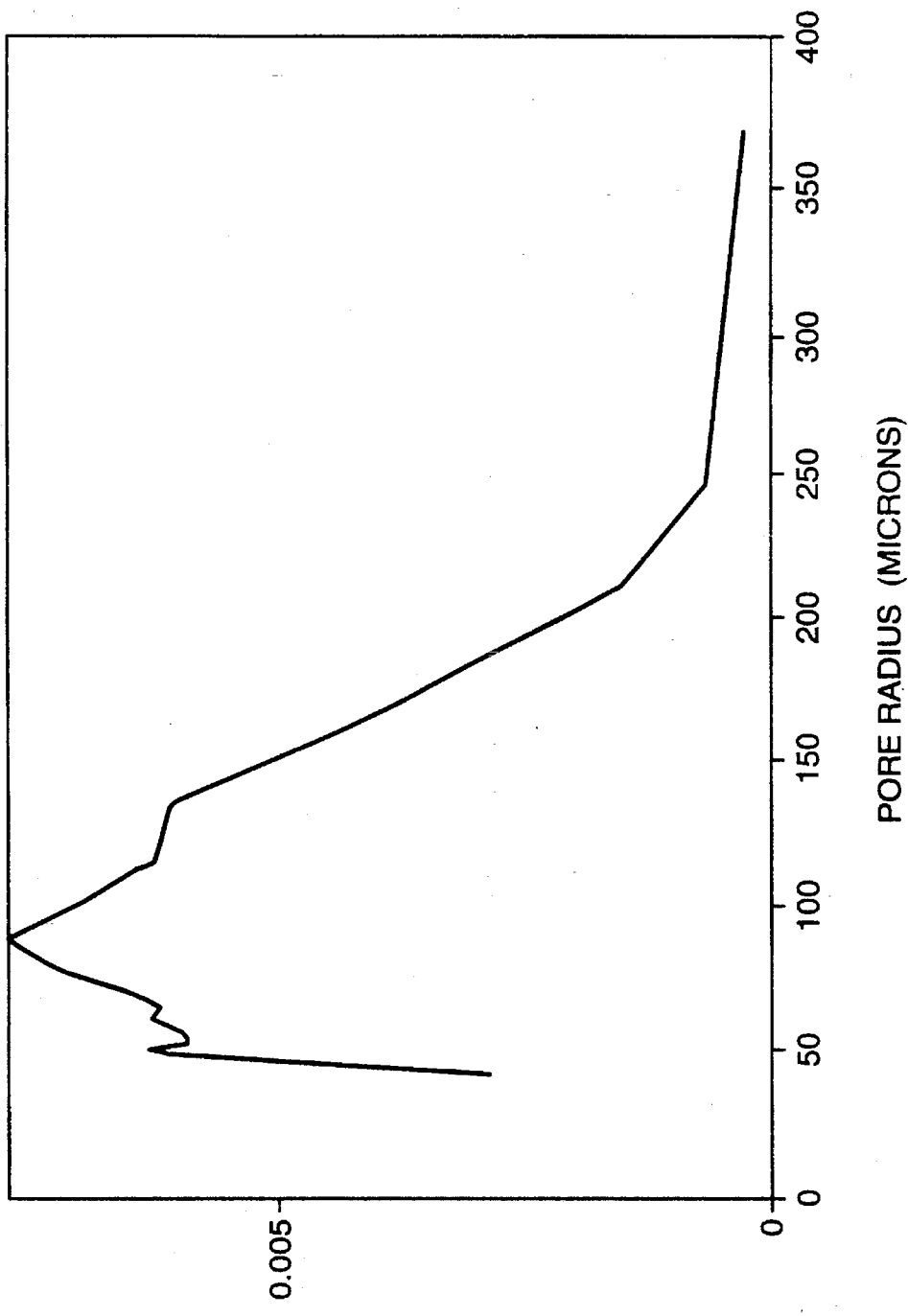
FIG. 1a presents the pore size distribution in the receiving layer measured by Gravimetric Absorbency Tester.

There are many methods and machines for forming nonwoven structures or webs, however, the transverse webber is the state of the art machine. A transverse webber can produce an integrated absorbent structure comprising pulp and fiber. Detailed descriptions of transverse webber apparatus and various methods for forming nonwoven structures or webs are known in the art and disclosed, for example, in U.S. Pat. Nos. 4,931,357, 4,927,685 and 4,921,659, all of which are incorporated herein by reference and are commonly assigned to the assignee of the present invention. Another apparatus for forming three dimensional shaped composite webs is disclosed in U.S. Pat. No. 5,076,774. Still another transverse web forming apparatus is disclosed in U.S. Pat. No. 4,952,128. A transverse pocket forming machine and method for use thereof is disclosed in U.S. Pat. No. 4,915,897. Despite the numerous methods and machines available, a significant problem with the state of the art machines is that they have a limited capability of handling superabsorbent (SA) powder or fibers which are generally essential for a thin absorbent product.

One embodiment of the present invention is a process that utilizes a web-forming apparatus to form an absorbent composite having contiguous density and fluid affinity gradients. Utilizing a web-forming apparatus, this process includes the step of increasing the amount of pulp fed into the web-forming apparatus relative to the amount of fiber fed into the web-forming apparatus, such that the composite produced has at least three layers with inter- and intralayer density gradients. In such a composite, the amount of pulp relative to the amount of fiber continuously increases from top to bottom of the absorbent composite.

While the process disclosed herein is useful in various web-forming machinery, a preferred embodiment utilizing a transverse webber will be described herein in detail for purposes of illustration. The present detailed disclosure is to be considered an exemplification of the principles of the invention and is not intended to limit the invention to this illustrative embodiment.

As disclosed in the references listed above, a transverse webber is a web-forming apparatus having two lickerins that feed materials into the machinery; one lickerin feeds pulp and the other feeds fiber. A strong vacuum draws material sequentially from the lickerins on to a conveyor belt. The side of the structure adjacent the conveyor belt becomes the top side of the absorbent composite.

As mentioned above, one embodiment of this invention provides a process for forming an absorbent composite that utilizes a transverse webber to form a layered absorbent composite having contiguous density and fluid affinity gradients. Such a composite may be formed by varying the relative amount of pulp and fiber feeding introduced to the lickerins along the length of each lickerin such that the amount of pulp fed into the pulp lickerin increases along the length of the pulp lickerin relative to the amount of fiber fed into the fiber lickerin along the length of the fiber lickerin. The amount of pulp and fiber introduced into the lickerins is varied such that the amount of pulp relative to the amount of fiber is different in at least three layers of the composite produced, and the amount of pulp relative to the amount of fiber continuously increases from top to bottom of the composite. The composite of the present invention may be incorporated into an absorbent structure by fusing the composite in an oven and then moisturizing the composite by spraying water on its surface, prior to coating the surface with superabsorbent and/or applying a layer of tissue. The absorbent composite is then calendared under a set of heated calendar rolls with a temperature below the melting point of the binding fibers.

The processes of the present invention therefore not only fully materialize the uniqueness of transverse webber technology, but also provide further improvements by incorporating superabsorbent, water spray and densification into the manufacturing system to generate an integrated absorbent structure having enhanced density and wettability gradients. Such an absorbent structure effectively distributes body fluids and utilizes storage capacity efficiently.

Figure 1B:

Thus, in a preferred embodiment, in the first section along the length of the lickerins, only fiber is fed into the lickerins. Although, the vacuum still draws a significant amount of pulp into its matrix, the amount of fiber is high relative to the amount of pulp. The amount of pulp drawn into the top section has minimum impact on the veneer stability of the composite but dramatically improves the veneer wettability. This wettability promotes flow of fluid through this top layer thereby providing a relatively dry surface. Accordingly, this thin, fiber rich, top section of the composite can serve as an efficient in-situ facing as well as a transfer layer (hereinafter this section will be referred to as the "transfer layer"). The amount of pulp relative to the amount of fiber fed into the lickerins is increased along the length of the lickerins such that the middle of the composite formed by this process comprises a thick pulp and fiber region having a medium fluid affinity and medium recovery (hereinafter this section will be referred to as the "receiving layer"). FIG. 1a illustrates the pore size distribution in a sample receiving layer measured by Gravimetric Absorbency Tester and FIG. 1b a cross section of the receiving layer measured. The difference between large and small pores could be more than eight folds. The pore size reduction along with pulp content increment from top to the bottom of the receiving layer directs liquid into the absorbent structure.

The amount of pulp relative to the amount of fiber fed into the lickerins continues to be increased along the length of the lickerins such that in the final section of the lickerins, the amount of pulp fed into the lickerins is high relative to the amount of fiber. As a result, the bottom side of the composite formed by this process has a high pulp content relative to the fiber content. This bottom layer comprising a densified pulp with a high fluid affinity, good capillary forces and minimal recovery provides the composite with good storage and wicking capabilities (hereinafter this section will be referred to as the "wicking layer").

The amount of pulp and fiber fed into the lickerins may be adjusted to provide a composite product having the following suggested ranges of average density, weight distribution and fiber content in each layer:

|  | Density Content (g/cc) | Weight Dist. | Fiber (%) |
| --- | --- | --- | --- |
| Transfer Layer | 0.1–1.2 | 5–15 | 99–80 |
| Receiving Layer | 0.002–0.15 | 30–75 | 30–5 |
| Wicking Layer | 0.1–0.4 | 50–15 | 10–1 |

Suitable fibers for use in this process include any fusible fiber with a homopolymer or copolymer (single component or bicomponent), with or without a wetting agent. Any blend of fusible fiber with synthetic and natural fibers may be employed, for example, polyethylene (PE), PE/PET Bico, PP, PET, acrylic, nylon, PE/PP Bico, nylon/nylon Bico, rayon, cotton, or synthetic pulp. In a preferred embodiment, the fiber comprises Enka Bico 1050, 3.0 denier, 1.5" length with a polyethylene sheath and PET core, commercially available from BASF. Suitable pulps for use in this process could be hardwood or softwood fluff pulps that are known in the art. In a preferred embodiment, the pulp is IP ELM Supersoft with a debonding agent, commercially available from International Paper. In other embodiments, staple fiber coils are used to replace carded webs.

In a particularly preferred embodiment, one 17 inch fiber web and two 8 inch fiber webs were produced on a inch card using this process. In this embodiment, the two 8 inch fiber webs are lined up from the operator side of the transverse webber with the 17 inch web and fed onto a pulp lickerin from the drive side via a pulp feed roll.

Figure 2:
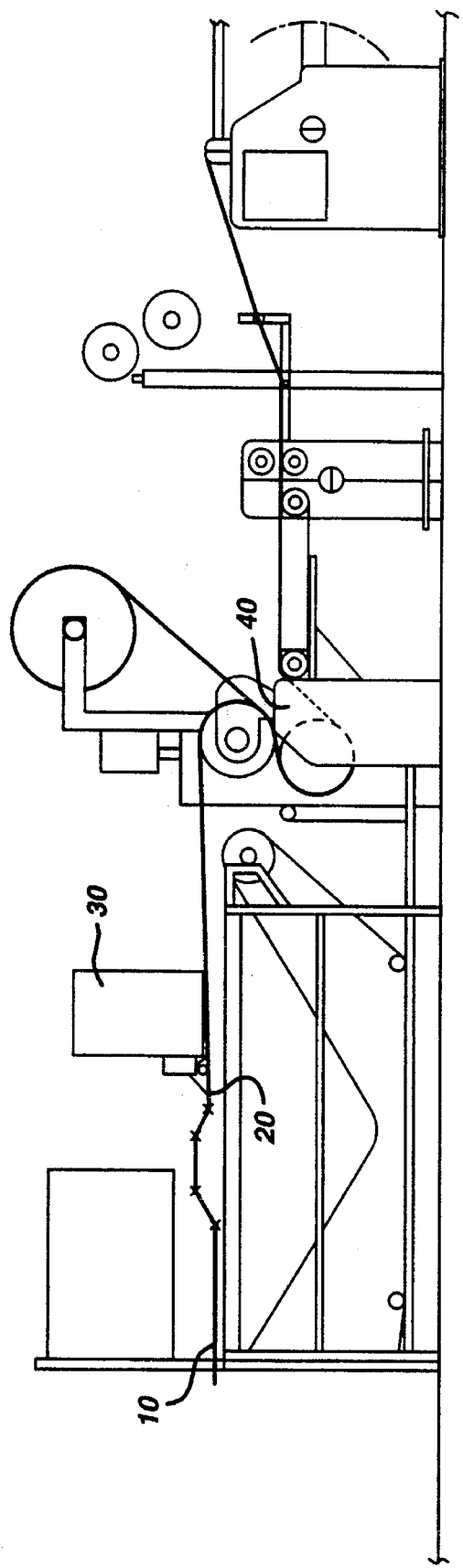
FIG. 2 illustrates a sliver from a transverse webber and oven 10, water sprayer 20, SA powder sprayer 30, 20 and a set of heated calendar rolls 40.

As noted above, the composite of the present invention is preferably incorporated into an absorbent structure by first fusing the composite produced (or sliver) through an oven and then moisturizing the sliver by spraying water on its surface before a coat of SA powder or fibers is applied and a tissue introduced. Referring to FIG. 2, in a preferred embodiment, the sliver from the transverse webber emerges from an oven 10 and is sprayed with water by water sprayer 20. Superabsorbent powder is then applied by an SA powder sprayer 30. The sliver is then calendared under a set of heated calendar rolls 40 with a temperature below the melting point of the binding fibers. The entire structure is calendared with heated rolls 40 that preferably have a temperature below the melting point of the binding fibers for densification and drying. The binding fibers may be, for example, thermoplastic fibers. Those of ordinary skill will be familiar with the operation of these devices.

The water that moisturizes the sliver is used to generate hydrogen bonding. The amount of hydrogen bonding at each level depends on the degree of water penetrating and pulp content in that region. The sliver then receives a coat of SA, for example, SA powder, from a dispenser. The SA powder is anchored by moisture on the sliver. The SA deposited on the sliver is very stable and the over-sprayed SA powder can be recycled, thereby eliminating SA waste in this process. Any SA powders or fibers are suitable for use herein. In a preferred embodiment, Sanwet IM-1000, commercially available from Hoechst-Celanese, is employed. A tissue is then introduced. Any tissues currently available and well known in the art having a basis weight of 0.2 to 2 osy are suitable. In a preferred embodiment, 0.6 osy, commercially available from Shawano Paper, is employed.

The amount of water and calendar pressure control the rate and total of absorbency and lateral wicking of the resulting structure. The moisture content may be varied from about 2 to 50 percent, preferably about 14 to 19 percent. The calendar pressure may be varied from about 20 to 1000 psi, preferably about 60 psi. Other process parameters which affect the quality of the product include, the lickerin speed, the vacuum, the oven temperature, the nose bar gap and the calendar role temperature. The lickerin speed for pulp may be varied from about 2000 to about 8000, preferably about 5000 rpm. The lickerin speed for fiber may be varied from about 1000 to about 5000 rpm, preferably about 3500 rpm. The vacuum is preferably from about 20 to 25 inches of water. The oven temperature may be varied from about 260 to about 350° F., preferably about 275° F. The nose bar gap for pulp may be set at from about 0.001" to about 0.01", preferably at 0.005" and the nose bar gap for fiber may be set at from about 0.001" to about 0.05", preferably at 0.015". The temperature of the calendar roll is below the melting point of the binding fibers. If, for example, PE thermoplastic fibers are employed, the temperature of the calendar roll is preferably about 250° F. The pulp slot opening, fiber slot opening and center plate position may also be varied. In a preferred embodiment, the pulp slot opening is 0 degrees, the fiber slot opening is 40 degrees and the center plate position is 14½ inches from the top.

Figure 3:
FIG. 3 shows a cross-section of a sample of an integrated absorbent structure.
Figure 4:
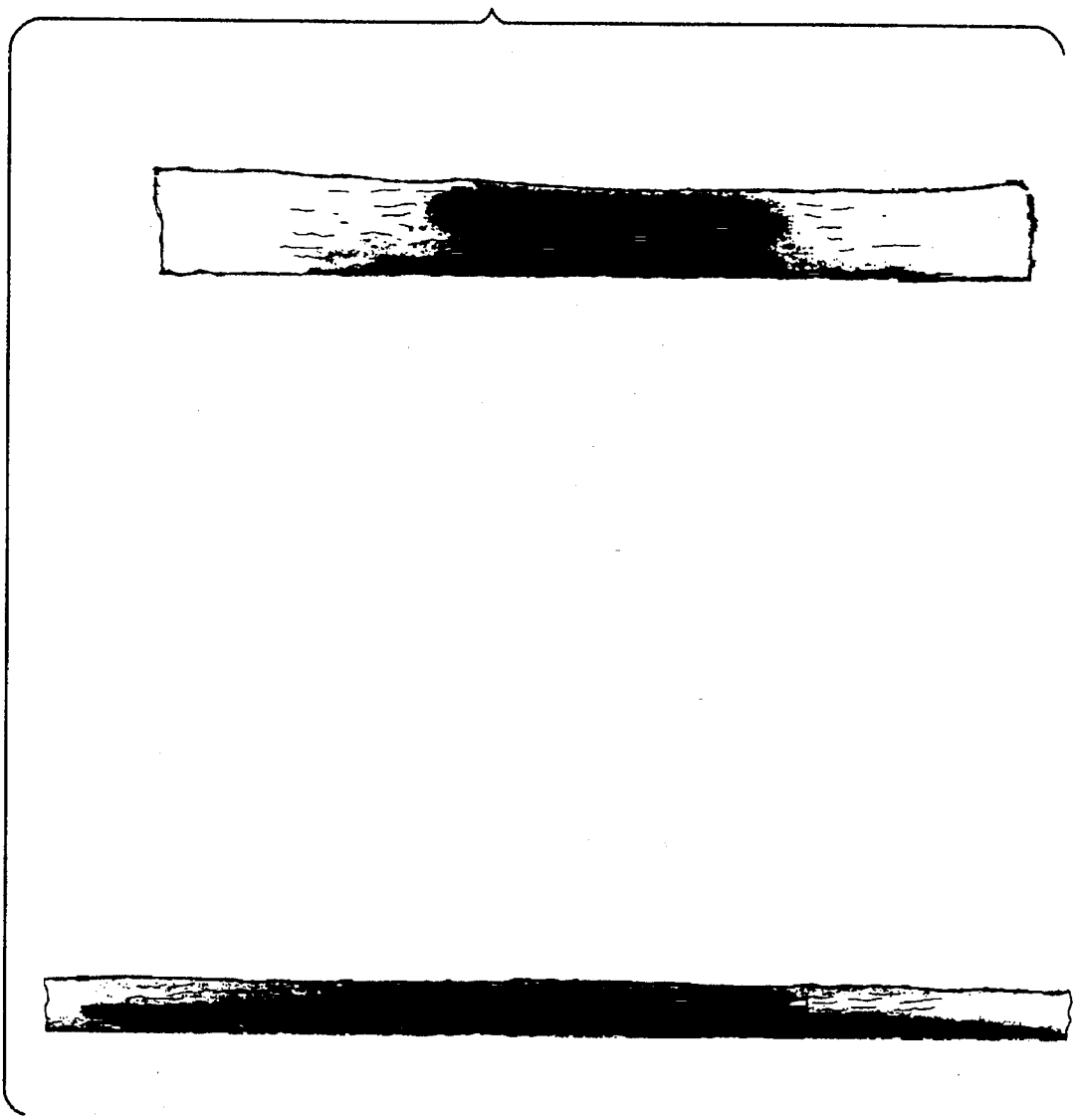
FIG. 4 demonstrates the flow pattern of SPTF3 fluid in the absorbent structure.

The continuous increase in the amount of pulp fed into the lickerins along its width relative to the amount of fiber provides a composite structure having at least three distinct density and liquid affinity gradients. As the pulp content continuously increases, the density increases. FIG. 3 shows a cross-section of a sample of an integrated absorbent structure. This figure demonstrates that the amount of pulp continuously increases from top to bottom of the sample structure. One significant advantage of such a structure is that as the density increases, the fluid affinity and capillary forces increase, thereby enabling the composite to quickly receive and move large amounts of fluid to the bottom of the structure to prevent wet feed and leakage. FIG. 4 demonstrates the flow pattern of SPTF3 fluid in the absorbent structure. It has a funnel shape and the top layer is almost free of fluid. A further advantage of this composite structure, is that fluid can only flow downward and cannot be retrieved under moderate pressure. In fact, pressing the composite actually helps the fluid in the upper structure drain to the bottom. When the pressure is released, the upper structure springs back but carries no fluid.

Another embodiment of the present invention provides an absorbent composite comprising at least three integrated regions with distinct density and fluid affinity gradients. The regions comprise a top transfer layer characterized as a thin, fiber rich region that is very wettable but does retain fluid and has good abrasion resistance, a middle receiving layer characterized as a thick pulp rich region with medium fluid affinity and medium recovery, and a bottom wicking layer characterized as a highly densified pulp region with a small percentage of fiber and having a high fluid affinity with minimal recovery. The amount of pulp relative to the amount of fiber in the various layers continuously increases from top to bottom of the absorbent structure such that the various layers have inter- and intralayer density gradients.

The suggested ranges of average density, weight distribution and fiber content in each layer is as follows:

|  | Density Content (g/cc) | Weight Dist. | Fiber (%) |
| --- | --- | --- | --- |
| Transfer Layer | 0.1–1.2 | 5–15 | 99–80 |
| Receiving Layer | 0.002–0.15 | 30–75 | 30–5 |
| Wicking Layer | 0.1–0.4 | 50–15 | 10–1 |

As the density of the composite increases from top to bottom, the fluid affinity and capillary forces increase thereby enabling the composite to quickly receive and move large amounts of fluid to the bottom of the structure to prevent leakage. In such a structure, fluid can only flow downward and cannot be retrieved under moderate pressure. Accordingly, pressing the composite actually helps the fluid in the upper structure drain to the bottom. When the pressure is released, the upper structure springs back but carries no fluid.

Figure 5:
FIG. 5 shows a cross-section of a sample of an integrated absorbent structure.

FIG. 5 shows a cross-section of a sample of an integrated absorbent structure. The weight distribution, pulp/fiber content, and density of each layer in this sample are also described. The picture illustrates that the pore size distribution in the transfer and wicking layers are relatively narrow. By contrast, the pore sizes in the receiving layer gradually reduces from top to the bottom and its distribution is much broader.

Figure 6:
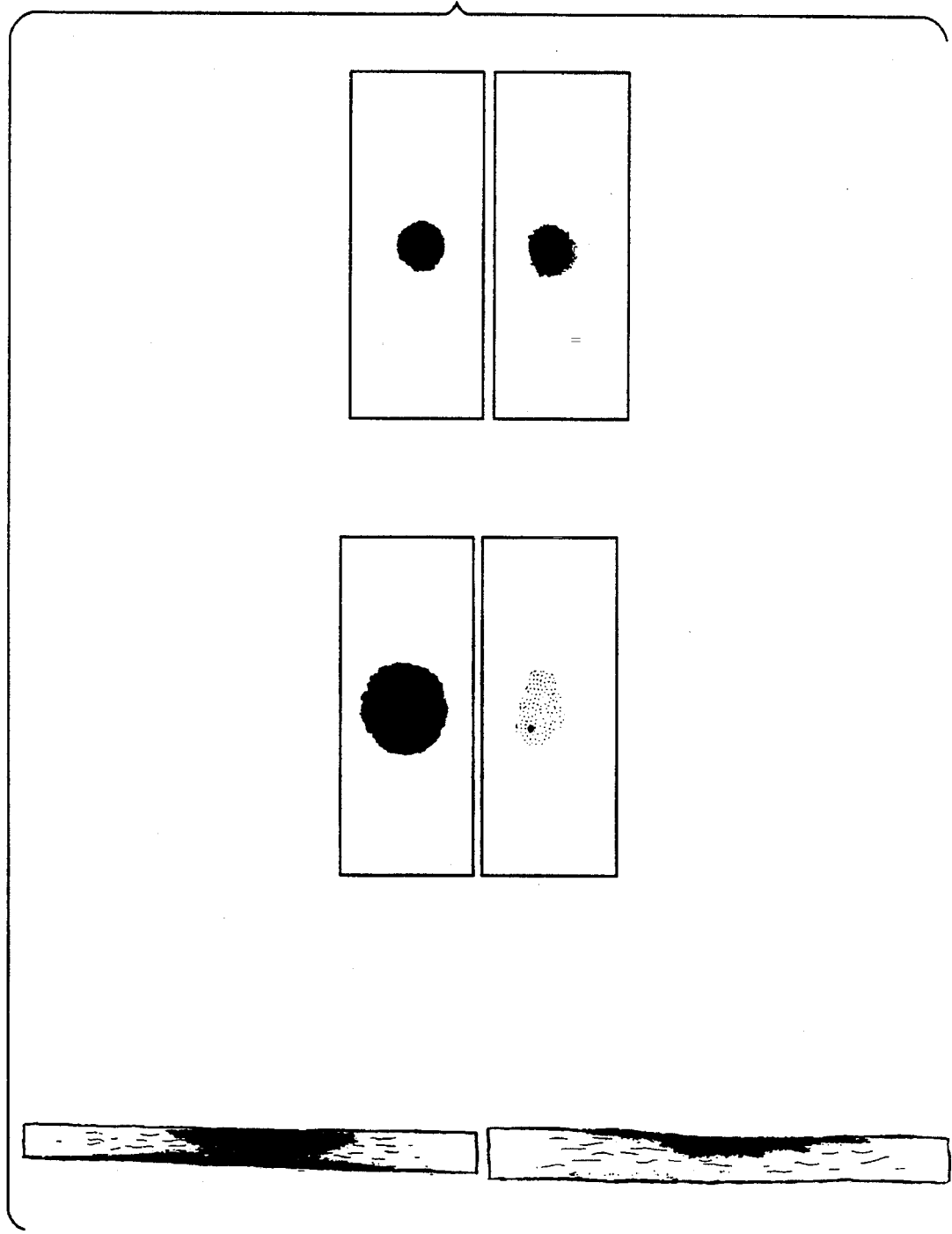
FIG. 6 shows two samples of the composite disclosed herein tested with 1.5 cc of SPTF3 fluid. The samples on the left were undisturbed but the samples on the right were carefully separated to three layers—transfer, receiving and wicking layers.

FIG. 6 shows two samples of the composite disclosed herein tested with 1.5 cc of SPTF3 fluid. The samples on the left were undisturbed but the samples on the right were carefully separated to three layers—transfer, receiving and wicking layers. The delaminated sample was compressed by hand before testing. The picture suggests that the integrated sample has no air gaps between layers to inhibit fluid flow.

An absorbent structure having a fourth layer comprising SA powder or fibers and tissue provided to the bottom of the composite described above is also provided herein. The region comprising the SA powder or fibers and tissue (hereinafter the "storage layer") is characterized as having the highest fluid affinity. The wicking layer and storage layer together provide the composite with efficient lateral wicking. An impermeable backing may also be provided to the bottom of the structure.

Figure 7A:
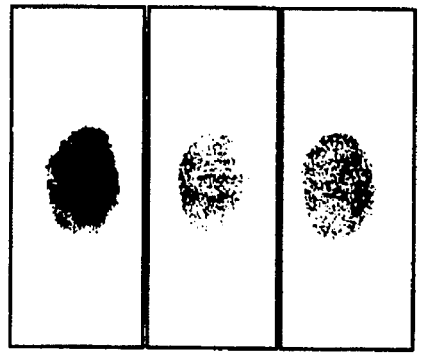
FIG. 7a is the front side and FIG. 7b the back side of three absorbent inserts tested with 5 cc of SPTF3 fluid. The insert shown on the left is a conventional insert with a densified layer and a nonwoven receiving layer, the insert in the middle is a sample of the composite disclosed herein without superabsorbent, and the insert on the right is the structure disclosed herein with superabsorbent.
Figure 7B:
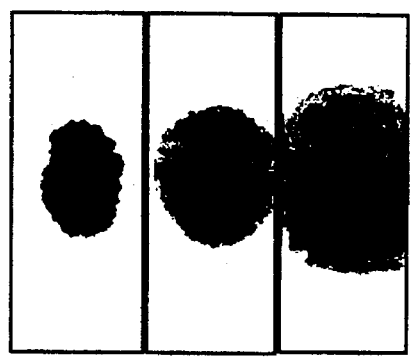

FIG. 7a is the front side and FIG. 7b the back side of three absorbent inserts tested with 5 cc of SPTF3 fluid. The insert shown on the left is a conventional insert with a densified layer and a nonwoven receiving layer, the insert in the middle is a sample of the composite disclosed herein without superabsorbent, and the insert on the right is the structure disclosed herein with superabsorbent. As the picture illustrates, the conventional absorbent insert has the same size of stain on both sides while in the composite and structure disclosed herein, the back stain is much larger than the front stain. The intensity of the front stain on the structure disclosed herein is lighter than the conventional insert.

Examples of suitable fibers, pulps, SA powders and tissues for use in forming absorbent composites and structures are provided in reference to a process disclosed herein. In a preferred embodiment, the absorbent composite is formed using a fiber comprising Enka Bico 1050, 3.0 denier, 1.511 length with a polyethylene sheath and PET core, commercially available from BASF, and the pulp is IP ELM Supersoft with a debonding agent, commercially available from International Paper. In a preferred embodiment, the absorbent structure is formed using the SA powder Sanwet IM-1000, commercially available from Hoechst-Celanese, and the tissue is 0.6 osy, commercially available from Shawano Paper.

I claim:

1. Utilizing a web-forming apparatus, a process for forming an absorbent composite having contiguous density and fluid affinity gradients wherein said process includes the step of increasing the amount of pulp fed into said web-forming apparatus relative to the amount of fiber fed into said web-forming apparatus, such that the composite produced has at least three integrated layers wherein the amount of pulp relative to the amount of fiber is different in each layer and the amount of pulp relative to the amount of fiber continuously increases from top to bottom of said absorbent composite.

2. Utilizing a transverse webber, a process for forming an absorbent composite having contiguous density and fluid affinity gradients wherein said process includes the step of increasing the amount of pulp fed into the pulp lickerin of said transverse webber along the length of said pulp lickerin relative to the amount of fiber fed into the fiber lickerin of said transverse webber along the length of said fiber lickerin such that the amount of pulp relative to the amount of fiber is different in at least three layers of the composite produced and the amount of pulp relative to the amount of fiber continuously increases from top to bottom of said absorbent composite.

3. The process according to claim 2 wherein the relative amounts of pulp and fiber are adjusted to provide said absorbent structure with a top layer, a middle layer, and a bottom layer, wherein the fiber content of the top layer comprises between about 80–99% of said top layer, the fiber content of the middle layer comprises between about 5–30% of said middle layer, and the fiber content of the bottom layer comprises between about 1–10% of said bottom layer.

4. The process according to claim 2 wherein the process further comprises the steps of:

(a) fusing said absorbent composite through an oven;

(b) moisturizing said absorbent composite by spraying water on its surface;

(c) applying a coat of SA powder or fibers to said absorbent composite;

(d) introducing a tissue to said absorbent composite; and (e) calendaring said absorbent composite under a set of heated calendar rolls with a temperature below the melting point of the binding fibers.

5. The process according to claim 4 wherein the water sprayed on said absorbent composite in step (b) is sprayed in an amount to provide said absorbent composite with a moisture content of between about 2 to 50 percent and wherein the calendar pressure applied in step (e) is between about 20 to 1000 psi.

6. The process according to claim 4 wherein the water sprayed on said absorbent composite in step (b) is sprayed in an amount to provide said absorbent composite with a moisture content of between about 14 to 19 percent and wherein said calendar pressure applied in step (e) is about 60 psi.

* * * * *